US00PP29942P3

(12) United States Plant Patent
Yencho et al.

(10) Patent No.: US PP29,942 P3
(45) Date of Patent: Dec. 4, 2018

(54) SWEETPOTATO PLANT NAMED 'NC05-198'

(50) Latin Name: ***Ipomoea batatas* (L.) Lam.**
Varietal Denomination: NC05-198

(71) Applicant: North Carolina State University, Raleigh, NC (US)

(72) Inventors: George Craig Yencho, Raleigh, NC (US); Kenneth Vincent Pecota, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 15/731,073

(22) Filed: Apr. 14, 2017

(65) Prior Publication Data

US 2018/0303020 P1 Oct. 18, 2018

(51) Int. Cl.
*A01H 5/06* (2018.01)

(52) U.S. Cl.
USPC ..... Plt./258

(58) Field of Classification Search
USPC ..... Plt./258, 226, 263.1, 256
CPC ... A01H 5/06; A01H 5/02; A01H 5/04; A01H 5/00; A01H 6/00
See application file for complete search history.

(56) References Cited

PUBLICATIONS

Barkley. Optimizing Cultural Management Practices and Consumer Acceptance of Sweetpotato in North Carolina 2015 thesis, retrieved on Apr. 10, 2018, retrieved from the Internet at https://repository.lib.ncsu.edu/bitstream/handle/1840.16/10171/etd.pdf?sequence=1, 4 introductory pages, p. 63. (Year: 2015).*

Progress Reports to the North Carolina Sweetpotato Commission. Title: Sweetpotato Breeding and Variety Development Support (2008), 24 pp.

Progress Reports to the North Carolina Sweetpotato Commission, Title: Sweetpotato Grower-Participatory Breeding Project Support (2008), 9 pp.

Progress Reports to the North Carolina Sweetpotato Commission, Title; Sweetpotato Breeding and Variety Development Support (2009), 25 pp.

Progress Reports to the North Carolina Sweetpotato Commission, Title: Sweetpotato Grower-Participatory Breeding Project Support (2009), 9 pp.

Progress Reports to the North Carolina Sweetpotato Commission, Title: Sweetpotato and Breeding and Variety Development Support (2010), 31 pp.

Progress Reports to the North Carolina Sweetpotato Commission, Title: Sweetpotato Grower-Participatory Breeding Project Support (2010), 13 pp.

Progress Reports to the North Carolina Sweetpotato Commission, Title: Sweetpotato Breeding and Variety Development Support (2011), 28 pp.

Progress Reports to the North Carolina Sweetpotato Commission, Title: Sweetpotato Grower-Participatory Breeding Project Support (2011), 12 pp.

Progress Reports to the North Carolina Sweetpotato Commission, Title: Sweetpotato Breeding and Variety Development Support (2012), 33 pp.

Progress Reports to the North Carolina Sweetpotato Commission, Title: Sweetpotato Grower-Participatory Breeding Protect Support (2012), 11 pp.

* cited by examiner

*Primary Examiner* — June Hwu
(74) *Attorney, Agent, or Firm* — Myers Bigel, P.A.

(57) ABSTRACT

*Ipomoea batatas* 'NC05-198' is a high yielding, orange fleshed, smooth skinned, rose-colored, table-stock sweetpotato. Plants from beds are early and storage root shape is generally not affected by cool planting conditions. 'NC05-198' produces uniformly shaped and sized roots resulting in a high pack-out of No. 1 roots by sweetpotato packers, giving it a high economic value. It is tolerant to internal necrosis. Based on multiyear disease evaluations, 'NC05-198 is resistant to fusarium wilt, moderately resistant to Streptomyces soil rot, and moderately susceptible to southern root knot nematode.

4 Drawing Sheets

Latin name of the genus and species: The Latin name of the novel plant cultivar disclosed herein is *Ipomoea batatas* (L.) Lam.

Variety denomination: This new and distinct sweetpotato cultivar of *Ipomoea batatas* (L.) Lam. has been given the denomination 'NC05-198'.

BACKGROUND OF THE INVENTION

*Ipomoea batatas* is a member of the morning glory family Convolvulaceae. This species is grown worldwide and it exhibits a wide range of plant forms and colors. Grown by farmers worldwide, the cultivated members of *Ipomoea*

*batatas* are commonly produced for consumption of their nutritious, enlarged storage roots. This contrasts with potatoes (*Solanum tuberosum*), which produce an edible tuber derived from an underground stem, which is similar in structure to the above ground stems.

Presently, two dominant sweetpotatoes are produced in the United States, 'Covington' (U.S. Plant Pat. No. 18,516) and 'Beauregard' (unpatented). 'NC05-198' provides an improvement over 'Covington' in that it produces plants that are ready earlier in the planting season, and does not produce round sweetpotatoes when planted in cooler soils. 'NC-05-198' is also tolerant to internal necrosis, a physiological defect in sweetpotato associated with the production of necrotic lesions in the internal portions of the storage root, which can be a significant problem in 'Covington' under certain conditions. 'NC05-198' provides an improvement over 'Beauregard' in consistency of shape and higher "pack-out" of the more valuable No. 1 class of sweetpotatoes and greater stability across different environments.

Lineage. 'NC05-198' originated from bulked botanical seed harvested from the open pollinated female parent 'NC97A-45' (not patented) in the 2004 Streptomyces soil rot (SSR) polycross breeding nursery. The SSR breeding nursery was planted in Clayton, Johnson County, N.C. (NC). The 15 genotypes present in the SSR nursery were randomly mated during the course of a four month flowering period in which seed was harvested from the 15 genotypes present in the nursery; therefore the male parent of 'NC05-198' is unknown. Three patented male parents ('L96-117' U.S. Plant Pat. No. 15,038, 'Bienville' U.S. Plant Pat. No. 15,380; and 'Evangeline' U.S. Plant Pat. No. 19,710) were in the nursery, and therefore, represent potential pollen sources.

Seedlings from the SSR breeding nursery were planted in greenhouses in Clinton, N.C. in March of 2005. A single cutting was taken from each seedling and planted in the field in May in Kinston N.C. and selected as a "single hill selection" on August 30$^{th}$. A "single hill selection" includes all of the good quality storage roots derived from the single plant cutting, typically 2-15 storage roots with 2-10 being saved for propagation the next year.

Asexual Reproduction. 'NC05-198' has been propagated as vegetative stem cuttings and/or storage root derived stem cuttings derived from adventitious sprouts emanating from its storage roots since its original selection in August of 2005. After further cycles of selection for horticultural traits and disease screenings, 'NC05-198' was subjected to meristem tip culture and subsequent tissue culture maintenance-to eliminate viruses and pathogens via meristem tip culture. The characteristics disclosed herein for 'NC05-198' have remained stable and the plant has reproduced true to type through successive generations of asexual propagation.

SUMMARY OF THE INVENTION

'NC05-198' is an orange-fleshed, smooth-skinned, light rose-colored table stock sweetpotato. 'NC05-198' produces yield equal to 'Covington' and 'Beauregard', the two main sweetpotato cultivars produced in the United States. The storage roots of 'NC05-198' tend to be longer than 'Covington' and similar in length to 'Beauregard', but more uniform in size and shape than 'Beauregard', producing a higher "packout" by sweetpotato packers. Plants from sprouted roots are ready 10 days to two weeks before 'Covington' and produce storage roots that are longer than 'Covington' when planted early in cooler soils, making 'NC05-198' more suited to earlier planting than 'Covington'. It is more resistant to internal necrosis compared to 'Covington' and is an option to growers who have problems with internal necrosis. The dry matter content is less than 'Covington' and similar to 'Beauregard'. The flavor of baked storage roots of 'NC05-198' has been judged to be excellent by standardized and informal taste panels. 'NC05-198' typically scores as well as or better than 'Covington' and 'Beauregard' for baking quality.

BRIEF DESCRIPTION OF THE DRAWINGS

The photographs in the drawings were made using conventional techniques and show the colors as true as reasonably possible by conventional photography. Colors in the photographs may differ slightly from the color values cited in the detailed botanical description, which accurately describe the colors of the new *Ipomoea batatas*.

DETAILED BOTANICAL DESCRIPTION OF THE NEW VARIETY

The following is a detailed description of the botanical characteristics of a new and distinct cultivar of *Ipomoea batatas* plant given the designation 'NC05-198'. All colors cited herein refer to The Royal Horticulture Society Colour Chart designations (The Royal Horticultural Society, London, 2001, 4$^{th}$ ed.) except where general terms of ordinary dictionary significance are used. Plant descriptions are based on the standardized international sweetpotato descriptors established jointly by the International Potato Center (CIP), Lima, Peru; The Asian Vegetable Research and Development Center (AVRDC), Taipei, Taiwan; and the International Board for Plant Genetics Resources (IBPGR), Rome, Italy (CIP, AVRDC, IBPGR. 1991. Descriptors for Sweet Potato. Huaman, Z., editor. International Board for Plant Genetic Resources, Rome, Italy, 134 pp.). Where dimensions, sizes, colors, and other characteristics are given, it is to be understood that such characteristics are approximations or averages set forth as accurately as practicable.

The descriptions and measurements of plant canopy reported herein were done on field grown plants 55 days after planting (DAP). The plants were grown in Clinton, N.C. The plants were grown under common commercial sweetpotato production practices during June through October. 'NC05-198' has not been observed under all possible environmental conditions; therefore, the phenotype may vary under different environmental conditions such as season, temperature, light intensity, day length, cultural conditions, and the like, without however, any variance in the genotype.

The following discussion provides a description of the new *Ipomoea batatas* 'NC05-198' with 'Beauregard' and 'Covington' for comparison. The female parent of 'NC05-198' was unavailable and remains unavailable for comparison.

Classification.

Botanical name: *Ipomoea batatas* (L.) Lam.

Common name: Sweetpotato

Variety name: 'NC05-198'

Figure 1:
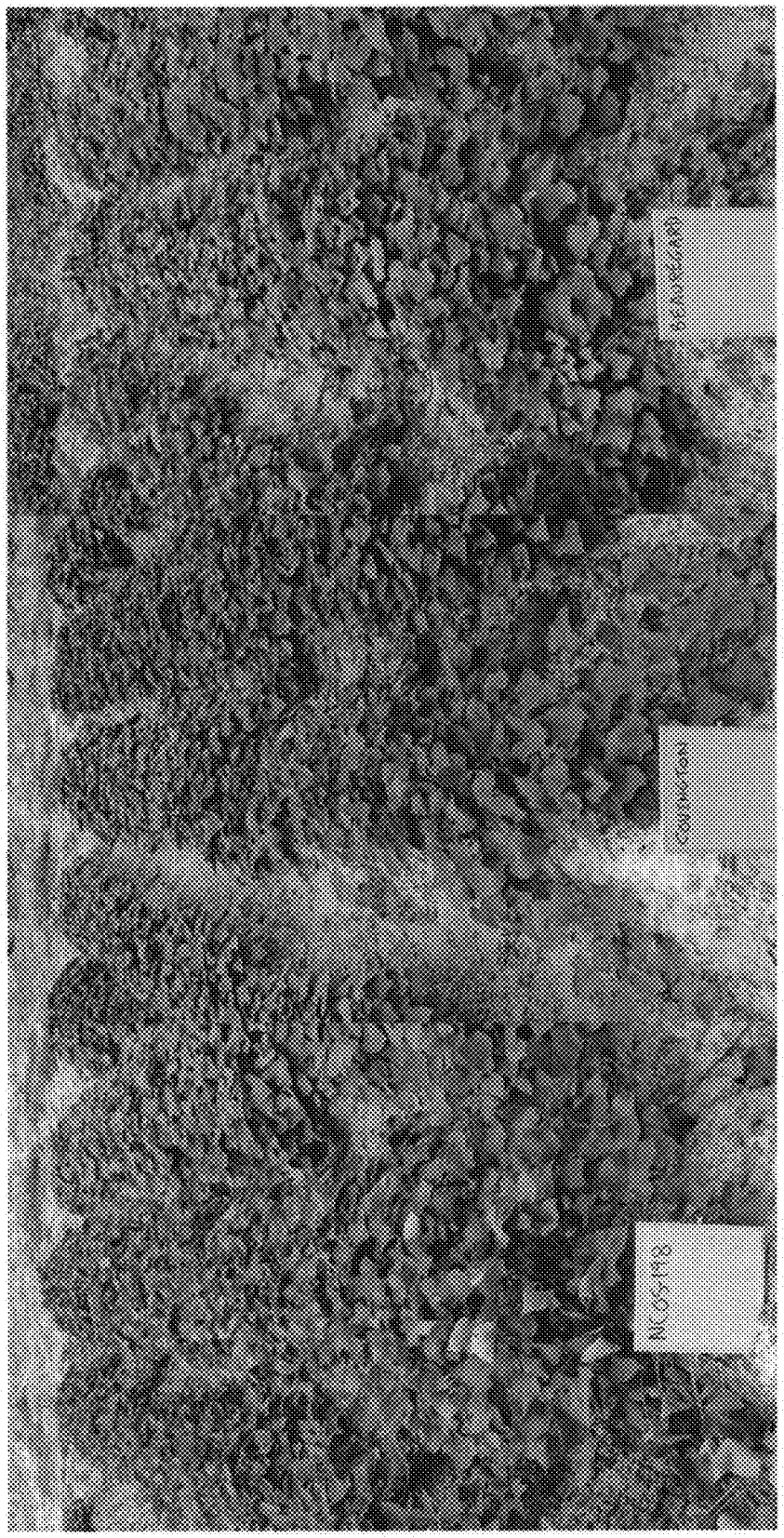
FIG. 1 is a color photograph of the above ground plant canopy produced by the new cultivar 'NC05-198', 'Covington' and 'Beauregard' 55 days after planting in Clinton, N.C. in 2015.

Growth Conditions Whole-plant Canopy Structure. FIG. 1 is a color photograph of the canopy biomass produced by the new variety 'NC05-198' and contrasted with 'Covington' and 'Beauregard'. Measurements were collected on field-grown plants at 55 DAP on 20 measurements per trait and recorded as the mean. 'NC05-198' and 'Covington' averaged two main vines, while 'Beauregard' averaged one, and mean main vine lengths were 84, 90, and 123 cm, respectively. The mean diameter at the base was 8, 8, and 7 mm, ('NC05-198' 'Covington', and 'Beauregard', respectively), and at 50 cm from the base of the main vine mean stem diameter was 5, 6, and 5 mm, respectively. 'NC05-198', 'Covington', and 'Beauregard' averaged five lateral branches per main vine, and stem color was green (144A, 144A to 144B, and 144A, respectively). The first internode length, beginning at the apex between the first and second fully expanded leaves, was 48 mm for 'NC05-198', 40 mm for 'Covington', and 59 mm for 'Beauregard'. 'NC05-198' appeared to have a denser canopy compared to 'Covington' and 'Beauregard', suggesting greater ground cover for potential weed suppression ability. Average height of 'NC05-198' is about 38 cm; however, this is a highly variable characteristic and dependent on soil moisture, fertility, plant age, and the like. Stem tip anthocyanin coloration for 'NC05-198' is weak and pubescence of the stem tip is sparse.

Figure 2A:
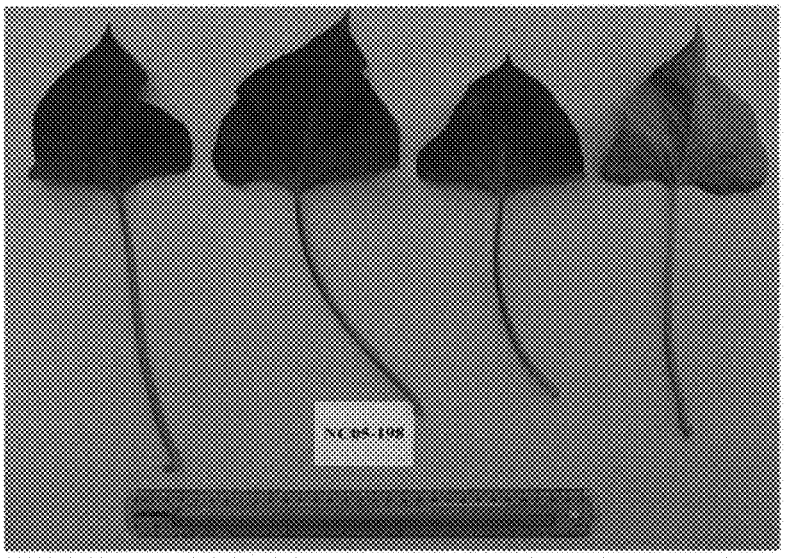
FIGS. 2A-2C are color photographs of typical mature leaves of 'NC05-198' (F1G. 2A), 'Covington' (FIG. 2B), and 'Beauregard' (FIG. 2C), 55 days after planting in Clinton, N.C. in 2015.
Figure 2B:
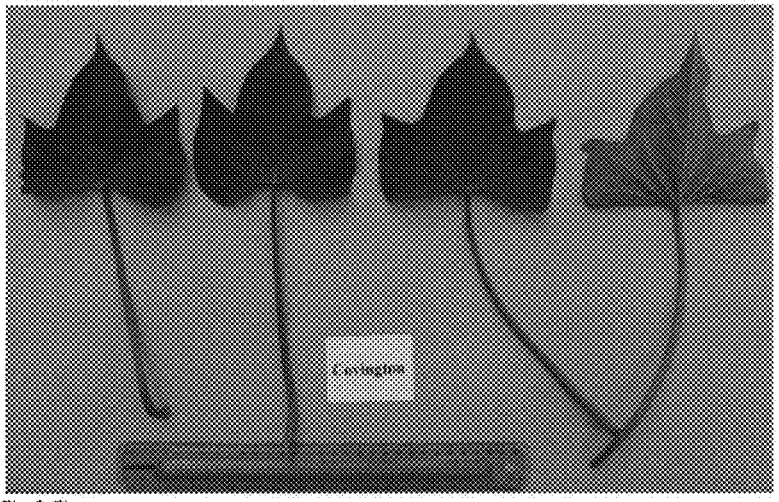
Figure 2C:
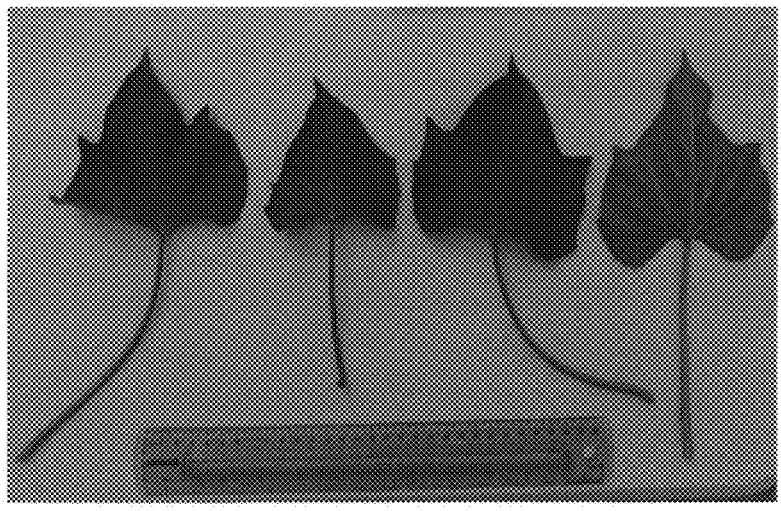
Figure 3A:
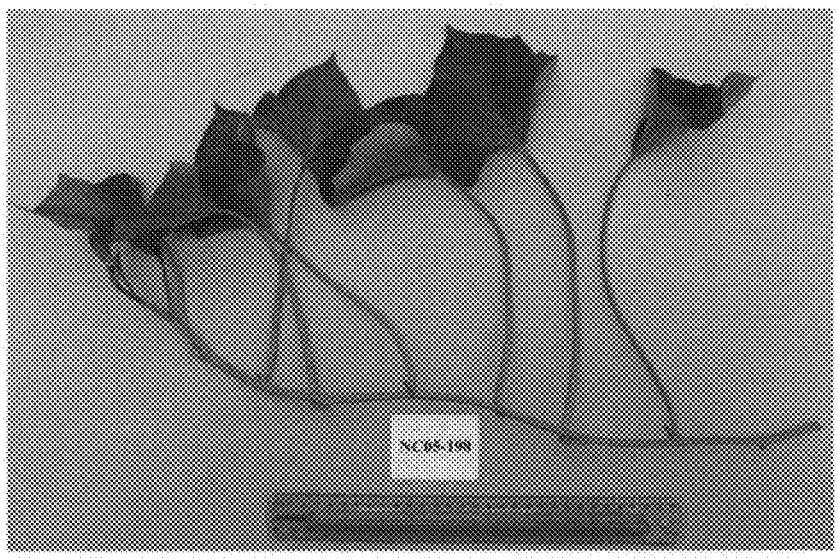
FIGS. 3A-3C are color photographs showing typical vines and the variety of leaves of 'NC05-198' (FIG. 3A). 'Covington' (FIG. 3B) and 'Beauregard' (FIG. 3C), 55 days after planting in Clinton N.C., in 2015.
Figure 3B:
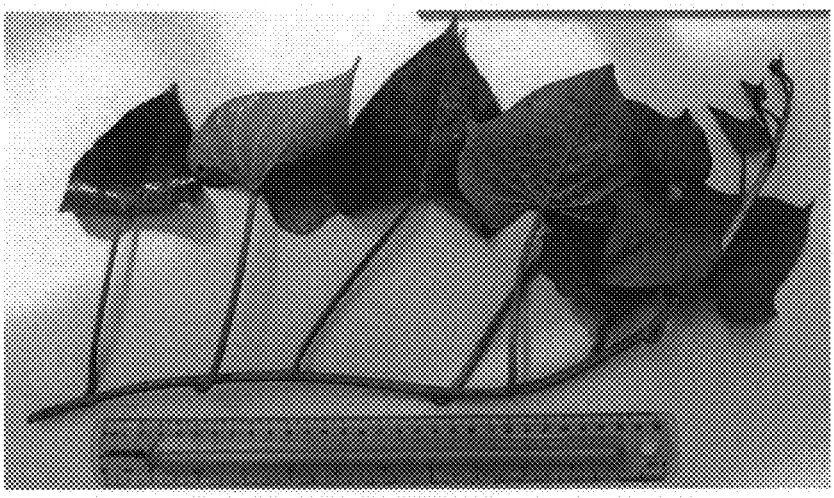
Figure 3C:
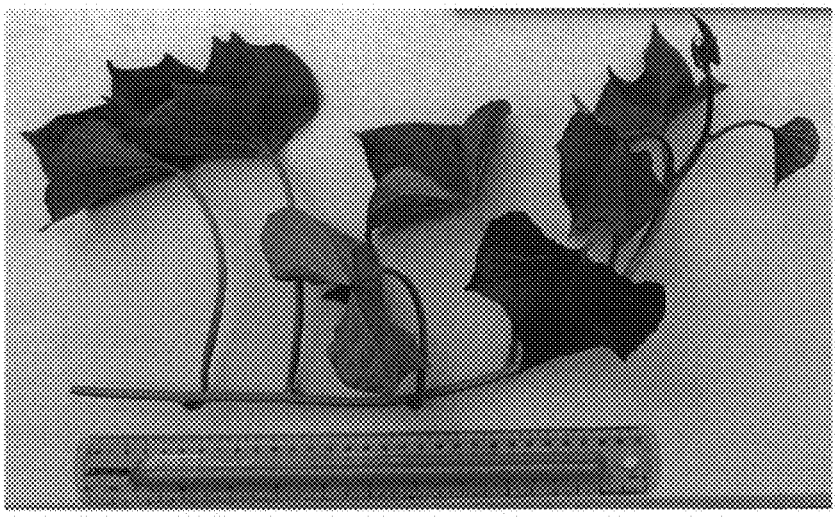

Foliage. The leaves of 'NC05-198' are alternate and simple in structure, and reniform to triangular in shape with no lobing (FIG. 2A and FIG. 3A). The leaves have a smooth texture and matte finish. Mature leaf color for 'NC05-198' 'Covington', and 'Beauregard' were green, 137A on the upper leaf surface and 147B on the lower surface. Young leaf color (upper and lower surfaces) displayed variation among the three cultivars: 'NC05-198' was 146A to 146B, 'Covington' was 146A with secondary purple (N77A), and 'Beauregard' was 146A with secondary purple (N77A); however, 'NC05-198' has slightly less purple pigmentation than 'Covington'. 'NC05-198' and 'Covington' were similar in mean leaf length (130 and 129 cm, respectively), while 'Beauregard' had the shortest length among the three cultivars (108 cm). Leaf width on average differed for all cultivars: 119, 139, and 122 cm ('NC05-198', 'Covington', and 'Beauregard', respectively). 'Covington' and 'Beauregard' have a purple spot (N77A) spot at the base of the main rib, while no pigmentation is present at the base of the main rib for 'NC05-198'. Petioles are green, 144A to 144B for 'NC05-198' and 144A for both 'Covington' and 'Beauregard'. Mean petiole length and diameter measured 206 and 5 mm for 'NC05-198', 189 and 5 mm for 'Covington', and 147 and 4 mm for 'Beauregard'.

Figure 4A:
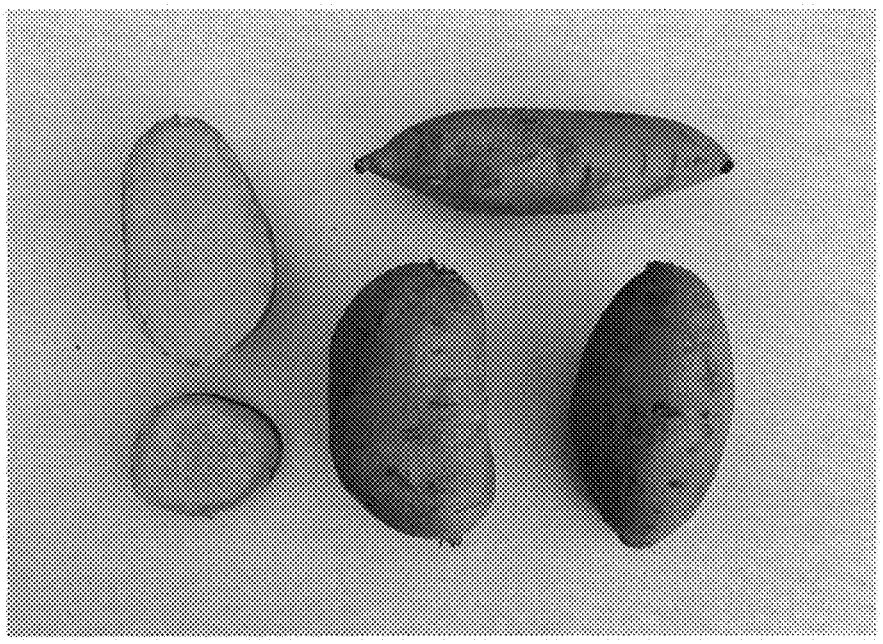
FIGS. 4A-4C are color photographs showing typical storage roots produced by 'NC05-198' (FIG. 4A), 'Covington' (FIG. 4B) and 'Beauregard' (FIG. 4C). The photographs were taken 107 days after harvest of the storage roots.
Figure 4B:
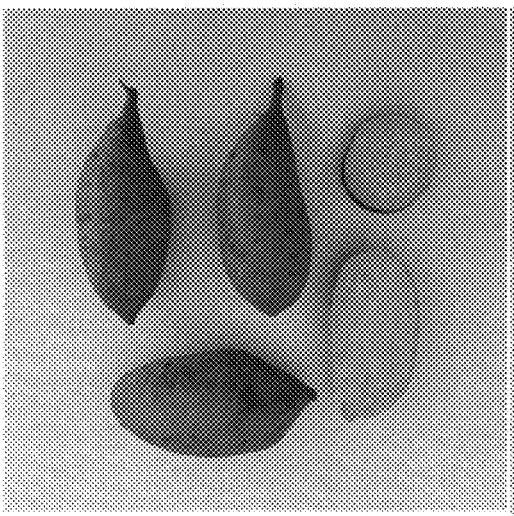
Figure 4C:
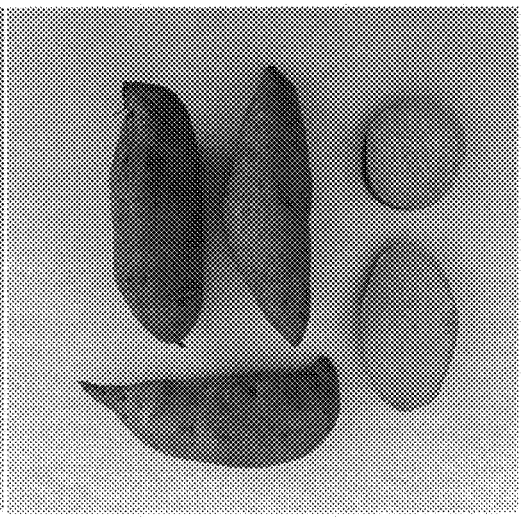

Storage Roots. 'NC05-198' produces orange fleshed (29A), smooth skinned, storage roots that are generally oblong to elliptic (FIG. 4A) having an average root diameter of about 2.4 in and root length of 5.2 in. The storage root cortex thickness of 'NC05-198' is medium (2-3 mm) and the depth of the eyes of the storage root is shallow. Storage root formation in 'NC05-198' is open cluster with the average number of storage roots per plant being about 5.4. The skin color of 'NC05-198' is light rose (34D to N170C), which is similar to 'Beauregard', and slightly less rose than 'Covington'. One of the more desirable attributes of 'NC05-198' is that it produces longer roots than 'Covington' for soils and conditions where 'Covington' roots can be more round. Storage roots of 'NC05-198' are generally longer than 'Covington' and similar in length to 'Beauregard'. Length to diameter ratios of storage roots in 31 trials over six years averaged 3.0, 2.7 and 2.1 for 'NC05-198', 'Beauregard' and 'Covington,' respectively. While the length is similar to 'Beauregard,' 'NC05-198' has fewer misshapes and a higher "packout" by sweetpotato packers. Carbohydrate profiles and β carotene levels are similar to 'Beauregard' and 'Covington', with all three being moist, sweet orange-fleshed types (Table 1).

TABLE 1

Carbohydrate and ß carotene profiles of NC05-198, Beauregard and Covington averaged over 21 trials in 2015 and 10 trials in 2014. Values are means with standard errors.

| Clone | % dry matter* | Starch* g/100 g dry weight | Fructose* g/100 g fresh weight | Glucose* g/100 g fresh weight |
|---|---|---|---|---|
| | | 2015 | | |
| NC05-198 | 19.2 ± 0.5 | 49.3 ± 1.6 | 0.52 ± .03 | 0.64 ± .04 |
| Beauregard | 17.6 ± 0.4 | 47.8 ± 1 5 | 0.67 ± .07 | 0.84 ± .09 |
| Covington | 19.2 ± 0.4 | 44.8 ± 1.7 | 0.42 ± .03 | 0.52 ± .04 |
| | | 2014 | | |
| NC05-198 | 17.2 ± 0.3 | 47 ± 2.3 | 0.38 ± 0.14 | 0.53 ± 0.17 |
| Beauregard | 16.4 ± 0.6 | 42.4 ± 4.2 | 0.52 ± 0.19 | 0.63 ± 0.21 |
| Covington | 18.1 ± 0.5 | 49.7 ± 2.8 | 0.42 ± 0.12 | 0.55 ± 0.14 |

| Clone | Sucrose* g/100 g fresh weight | Total sugars* g/100 g fresh weight | ß carotene* mg/g dry wt |
|---|---|---|---|
| | | 2015 | |
| NC05-198 | 1.40 ± 0.1 | 2.55 ± 0.12 | 0.40 ± .02 |
| Beauregard | 0.61 ± .08 | 2.12 ± 0.18 | 0.38 ± .02 |
| Covington | 1.9 ± .13 | 2.85 ± 0.15 | 0.42 ± .02 |
| | | 2014 | |
| NC05-198 | 1.68 ± 0.25 | 2.60 ± 0.25 | — |
| Beauregard | 2.00 ± 0.13 | 3.15 ± 0.3 | — |
| Covington | 1.74 ± 0.22 | 2.68 ± 0 17 | — |

*Values are predictions using NIRS calibrations developed by the NCSU Sweetpotato Breeding Program Storage Root Yield. Yield comparisons of 'NC05-198' are with 'Covington' and 'Beauregard', the two major sweetpotato cultivars grown in the United States. The yield trials are split into two groups based on virus-indexed status. One group contains the comparisons where 'NC05-198' is seed stock that was not meristemmed and virus indexed, and would be G4-G7 (four to seven generations of field exposure since being free from virus) Table 2. Table 3 compares crops produced from virus-indexed seed G2-G3 with the checks. The checks in the yield trials are always G2 or G3 stock. Comparing G2 checks to G4-G7 stock can be misleading since virus accumulation will affect both yield and quality (packout of No .1's, canners, jumbo's and culls). In the 12 trials comparing G2 and G3 stock of 'NC05-198', 'Beauregard' and 'Covington', 'NC05-198' was significantly different (p=0.05) than 'Beauregard' (B94-14) in six of those trials, and significantly different (p=0.05) than 'Covington' in two of the trials. In all instances where there was a significant difference, 'NC05-198' had higher total marketable yield.

TABLE 2

Average performance of NC05-198(G4-G7), Covington G2 and B94-14 G2 Beauregard over 18 yield tests, 2008-2011.

| | Total Yield | Marketable Yield | | |
|---|---|---|---|---|
| CLONE | bu/A | Bu/A | % Beau | % Cov |
| NC05-198 G4-G7 | 971 | 809 | 98 | 96 |
| Covington G2 | 946 | 890 | 110 | |
| Beauregard G2-3 (B94-14) | 1021 | 851 | | 101 |

| | Size Distribution by Class (% of total yield) | | | | No. 1 50 lb |
|---|---|---|---|---|---|
| CLONE | No. 1's | Canners | Jumbo's | Culls | bu/ac |
| NC05-198 G4-G7 | 53 | 14 | 15 | 17 | 431 |
| Covington G2 | 58 | 14 | 23 | 6 | 513 |
| Beauregard G2-3 (B94-14) | 43 | 12 | 28 | 17 | 369 |

TABLE 3

Average performance of NC05-198 G2-3, Covington G2-3 and B94-14 CM Beauregard over 12 yield tests, 2014-2015.

| | Total Yield | Marketable Yield | | |
|---|---|---|---|---|
| CLONE | bu/A | bu/A | % Beau | % Cov |
| NC05-198G2-3 | 1130 | 1032 | 132 | 122 |
| Covington G2-3 | 956 | 865 | 113 | . |
| Beauregard G2-3 (B94-14) | 996 | 825 | . | 98 |

| | Size Distribution by Class (% of total yield) | | | | No. 1 50 lb |
|---|---|---|---|---|---|
| CLONE | No. 1's | Canners | Jumbo's | Culls | bu/ac |
| NC05-198G2-3 | 60 | 14 | 17 | 9 | 620 |
| Covington G2-3 | 55 | 16 | 19 | 9 | 479 |
| Beauregard G2-3 (B94-14) | 44 | 12 | 27 | 18 | 359 |

US #1 's - Roots 2" to 3½" diameter, length of 3" to 9", must be well shaped and free of defects.
Canners - Roots 1" to 2" diameter. 2" to 7" in length.
Jumbos - Roots thai exceed the diameter, length and weight requirements of the above two grades,
but are of marketable quality.
Percent US #1's - Calculated by dividing the weight of US HVs by the total marketable weight (Culls
not included).
Culls - Roots must be 1" or larger in diameter and so misshapen or unattractive that they could not fit
as marketable roots in any of the above three grades.

Disease or Pest Resistance. Table 4, below, summarizes the results of disease evaluations of 'NC05-198'. Based on multiyear disease evaluations, 'NC05-198 is resistant to Fusarium wilt (Fusarium oxysporum Schlect. f. sp. batatas (Wollenw.) Snyd. & Hans.), moderately resistant to Streptomyces soil rot, Streptomyces ipomoeae (Person & W. J. Martin) Waksman & Henrici) and moderately susceptible to southern root knot nematode, Melodogyne incognita (Kofoid & White). The Fusarium resistance of 'NC05-198' is similar to 'Covington,' which is important since there is no cultural control. The moderate resistance of 'NC05-198' to Streptomyces is slightly less than that observed for 'Beauregard' or 'Covington', but is still sufficient for moderate protection. Root knot nematodes will need to be controlled similar to 'Beauregard'.

'NC05-198' is susceptible to the WDS (wireworm, Diabrotica, Systena) complex of insects, which are the major causes of insect damage in sweetpotato in North Carolina.

TABLE 4

Disease screen results for NC05-198, Beauregard and Covington over seven years for Southern root-knot nematode (*Meloidogyne incognita*) (Kofoid & White), fusarium wilt (*Fusarium oxysporum* schect. f. sp. batatas (Wollenw.) Snyd. & Hans.), and Streptomyces soil rot (*Streptomyces ipomoeae* (Person & W. J. Martin) Waksman & Henrici)

| NC05-198 | 2014 | 2012 | 2011 | 2010 | 2009 | 2008 | 2007 | Average |
|---|---|---|---|---|---|---|---|---|
| Root-knot nematode | MS | MR | S | MS | MS | MS | — | MS |
| Fusarium wilt | R | MR | R | MR | R | MR | R | R |
| SSR-GH | R | R | MR | R | MR | MR | MS | MR |
| SSR-field | R | MR | MR | R | R | MR | H | MR-R |
| Covington | | | | | | | | |
| Root-knot nematode | R | R | R | HR | R | R | — | R |
| Fusarium wilt | R | R | R | R | R | R | R | R |
| SSR-GH | MR | R | R | MS | R | R | R | MR-R |
| SSR-field | R | R | R | R | R | R | R | R |
| Beauregard | | | | | | | | |
| Root-knot nematode | HS | S | HS | MS | HS | HS | — | HS-S |
| Fusanum wilt | MR | R | R | MR | MR | R | R | MR-R |
| SSR-GH | R | MR | R | R | R | R | R | R |
| SSR-field | R | MR | R | MR | R | R | R | R |

Scale - HS - highly susceptible, S - susceplible, MS - moderately susceptible- MR - moderately resistant
R - resistant, HR - highly resistant
The root knot nematode rating is based on the number of galls on roots counted eight weeks after inoculation with 10,000 eggs of *M. incognita* race 3 in plants established in four inch pots. Gall count classes: HR = 0; R = 1-3; MR = 4-10; MS = 11-30; S = 31-100; HS = 101+ galls. 4 reps.
The Fusarium wilt rating involves dipping fresh cue plants in a solution of *Fusarium oxysporum* spores then rating for mortality and vascular tissue browning. 3 reps of five plants each are used.
Streptomyces soil rot is screened in both the greenhouse and field. The greenhouse trial involves planting slips into media that is a mix of sand and vermiculite media on which the bacteria is raised. Rating is done 8-10 weeks after planting on damage to fibrous roots. The field trial is in a field with high levels of SSR pressure. Plots are rated for both fibrous root damage, yield and storage root lesions.

Internal Necrosis. Table 5, below, shows the results of a screening for internal necrosis (IN), a physiological disorder that can be a serious storage root production problem in 'Covington'. It is dead tissue inside the sweetpotato typically expressed on the proximal end of a storage root. Internal necrosis is undetectable from the outside of the storage root so it can't be picked off a grading line. 'Covington' appears to be susceptible under certain conditions, though these conditions have not yet been clearly defined. It is known that application of ethephon to the plant foliage prior to harvest, a treatment used to toughen the skin, will enhance IN in many sweetpotato cultivars. This is used as a screen to identify tolerant clones, 'NC05-198' has shown tolerance even when treated with ethephon. This makes it a good option where growers are having a problem with IN in 'Covington'.

TABLE 5

Internal Necrosis severity ratings and incidence among commercial sweetpotato cultivars treated with and without Ethephon at Jones Farm in 2014.

| | no prep | | | prep | | |
|---|---|---|---|---|---|---|
| Clone | % Incidence | Average Severity[1] | Avg. # Roots Cut | % Incidence | Average Severity[1] | Avg. # Roots Cut |
| Beauregard | 0 | 0.0 | 24 | 1 | 0.3 | 25 |
| Covington | 68 | 2.8 | 24 | 81 | 3.0 | 25 |

TABLE 5-continued

Internal Necrosis severity ratings and incidence among commercial sweetpotato cultivars treated with and without Ethephon at Jones Farm in 2014.

| | no prep | | | prep | | |
|---|---|---|---|---|---|---|
| Clone | % Incidence | Average Severity[1] | Avg. # Roots Cut | % Incidence | Average Severity[1] | Avg. # Roots Cut |
| Evangeline | 3 | 1.0 | 25 | 1 | 0.7 | 25 |
| Hatteras | 27 | 2.1 | 24 | 49 | 2.8 | 26 |
| Hernandez | 0 | 0.0 | 25 | 1 | 0.3 | 23 |
| Bellevue | 0 | 0.0 | 25 | 0 | 0.0 | 25 |
| Burgundy | 7 | 1.2 | 24 | 0 | 0.0 | 24 |
| NC05-198 | 0 | 0.0 | 25 | 0 | 0.0 | 24 |
| Orleans | 0 | 0.0 | 25 | 8 | 1.2 | 25 |
| means | 11.6 | 0.8 | 24.7 | 15.8 | 0.9 | 24.6 |

Average severity is basal upon 0-4 severity scale with ratings of 3 to 4 being unmarketable.
3 reps used in the trial.

Storage ability of 'NC05-198' is good, though it is not recommended for long-term storage. Depending on harvest conditions, there may be some pithiness present 6-8 months after storage.

Flood tolerance of 'NC05-198' is similar to 'Covington' under wet conditions. 'Covington' is considered tolerant to wet conditions, though any cultivar will be lost if submerged. 'NC05-198' will show a proliferation of lenticels under very wet conditions.

We claim:

1. A new and distinct cultivar of *Ipomoea batatas* plant named 'NC05-198', substantially as illustrated and described herein.

* * * * *